(12) United States Patent
Eder (10) Patent No.: US 9,615,841 B2
(45) Date of Patent: Apr. 11, 2017

(54) DEVICE FOR MAKING A BOREHOLE INTO A BONE

(75) Inventor: Klaus Eder, Perchtoldsdorf (AT)

(73) Assignee: JEDER GMBH, Vienna (AT)

( * ) Notice: Subject to any disclaimer, the term of this patent is extended or adjusted under 35 U.S.C. 154(b) by 202 days.

(21) Appl. No.: 13/126,649

(22) PCT Filed: Oct. 20, 2009

(86) PCT No.: PCT/AT2009/000410
§ 371 (c)(1),
(2), (4) Date: Jul. 6, 2011

(87) PCT Pub. No.: WO2010/048648
PCT Pub. Date: May 6, 2010

(65) Prior Publication Data
US 2011/0270236 A1    Nov. 3, 2011

(30) Foreign Application Priority Data

Oct. 28, 2008 (AT) ................................ A 1680/2008
Dec. 10, 2008 (AT) ................................ A 1923/2008

(51) Int. Cl.
*A61B 18/20* (2006.01)
*A61B 17/16* (2006.01)
(Continued)

(52) U.S. Cl.
CPC ........ *A61B 17/176* (2013.01); *A61B 17/1673* (2013.01); *A61B 17/1688* (2013.01); *A61B 17/1785* (2016.11); *A61C 8/0089* (2013.01); *A61C 8/0092* (2013.01); *A61B 17/1633* (2013.01); *A61B 17/1695* (2013.01); *A61B 17/8805* (2013.01); *A61B 2017/00017* (2013.01); *A61B 2090/034* (2016.02); *A61B 2090/062* (2016.02); *A61B 2090/064* (2016.02)

(58) Field of Classification Search
CPC ............ A61B 17/1671; A61B 17/1617; A61B 17/176
USPC .................................................. 606/3, 80, 96
See application file for complete search history.

(56) References Cited

U.S. PATENT DOCUMENTS 5,098,435 A * 3/1992 Stednitz et al. ............... 606/916
5,403,276 A * 4/1995 Schechter ........ A61B 17/32002
604/118
(Continued)

FOREIGN PATENT DOCUMENTS

DE    10 2007 059226    6/2008
EP    1 269 933 A2     1/2003
(Continued)

*Primary Examiner* — Gary Jackson
*Assistant Examiner* — Amanda Steinberg
(74) *Attorney, Agent, or Firm* — Henry M. Feiereisen LLC (57) ABSTRACT

The invention relates to a device for penetratingly extending a blind hole into a hard tissue, particularly a jawbone. The device is characterized in that it comprises a tubular body (1) having a distal working opening (2) and an inlet (3) opposite the working opening (2), said inlet being closed by a sealing element (4) that is penetrated by a shaft (5) of a working tool, for example a milling tool (5, 6), and allows at least a feed motion, a drive motion and a steering motion of the working tool (5, 6), the tubular body (1) being provided with a connection (8) for applying an internal pressure.

14 Claims, 5 Drawing Sheets

(51) Int. Cl.
*A61B 17/17* (2006.01)
*A61C 8/00* (2006.01)
*A61B 17/88* (2006.01)
*A61B 17/00* (2006.01)
*A61B 90/00* (2016.01)

(56) References Cited

U.S. PATENT DOCUMENTS

| | | | |
|---|---|---|---|
| 5,993,458 A * | 11/1999 | Vaitekunas et al. | 606/104 |
| 6,358,252 B1 | 3/2002 | Shapira | |
| 6,716,215 B1 * | 4/2004 | David et al. | 606/80 |
| 2003/0055404 A1 * | 3/2003 | Moutafis | A61B 17/1633 604/540 |
| 2004/0191897 A1 * | 9/2004 | Muschler | 435/325 |
| 2005/0059905 A1 * | 3/2005 | Boock et al. | 600/567 |
| 2007/0016100 A1 * | 1/2007 | Miller | 600/567 |
| 2007/0265491 A1 * | 11/2007 | Krag et al. | 600/37 |
| 2009/0204158 A1 * | 8/2009 | Sweeney | 606/309 |
| 2010/0094297 A1 * | 4/2010 | Parmigiani | 606/80 |
| 2010/0121330 A1 * | 5/2010 | Parmigiani | 606/79 |
| 2011/0160781 A1 * | 6/2011 | Miller et al. | 607/3 |

FOREIGN PATENT DOCUMENTS

| | | |
|---|---|---|
| JP | 2007-313285 | 12/2007 |
| RU | 2 322 200 | 4/2008 |
| SU | 1253630 | 8/1986 |
| SU | 1309973 | 5/1987 |
| WO | WO 2007/129312 | 11/2007 |
| WO | WO 2009/000052 | 12/2008 |

\* cited by examiner

DEVICE FOR MAKING A BOREHOLE INTO A BONE

CROSS-REFERENCES TO RELATED APPLICATIONS

This application is the U.S. National Stage of International Application No. PCT/AT2009/000410, filed Oct. 20, 2009, which designated the United States and has been published as International Publication No. WO 2010/048648 and which claims the priority of Austrian Patent Applications, Serial No. A1680/2008, filed Oct. 28, 2008, and Serial No. A1923/2008, filed Dec. 10, 2008, pursuant to 35 U.S.C. 119(a)-(d).

BACKGROUND OF THE INVENTION

The invention relates to a device for penetratingly extending a blind hole introduced into hard tissue, particularly a jawbone.

Such extension of a bone bore is required, for example, in the field of dental surgery wherein performing a procedure referred to as "sinus lift". Sinus lift refers to a surgical procedure where the sinus mucous membrane is a partially detached from the jawbone and lifted to provide space between the bone and the sinus mucous membrane. Autologous bone (e.g., from tuber maxillae, linea obliqua, the chin region or from the iliac crest (bone replacement materials, bone chips)) or a synthetic bone replacement material (for example bone replacement material with the brand name Bio-Oss from the company Geistlich AG), frequently mixed with autologous bone, is introduced in the generated cavity. This material should transform itself into bone within six months so as to ensure a solid foundation for an implant.

The conventional approach with a sinus lift is to prepare a buccal mucoperiosteal flap in the molar region and to mill an oval window in the exposed bone without damaging the underlying sinus mucous membrane. The oval bone disk suspended from the sinus mucous membrane is then carefully pressed towards the maxillary antrum, while the sinus mucous membrane is simultaneously carefully detached from the bone around the window with special instruments. Because the sinus mucous membrane is very delicate, somewhat comparable to the skin of an egg, this process must be performed very carefully because of the risk of damage to the sinus mucous membrane. The cavity generated in this way in the maxillary antrum is now filled through the window with the bone replacement material and the buccal window is covered with a foil. The foil is typically made from a resorbable material, for example a membrane with the brand name Bio-Guide from the company Geistlich AG. The mucoperiosteal flap is then tightly stitched. The method is quite invasive and stresses the patient due to severe swelling and discoloration for up to 10 days, eventually also due to pain.

This surgical method is frequently also referred to as "open" or "classic" sinus lift. If sufficient residual bone height exists (approximately with the height of 5 mm), then implants can be inserted "simultaneously" with the sinus lift (one-time sinus lift). The implant can only be fully loaded after the bone replacement material has solidified. If the residual bone height is too thin, then the implants are inserted in a second procedure approximately 6-8 months after the sinus lift (two-time sinus lift).

A more recent method is the so-called crestal sinus lift which does not require opening a flap in a bone plate. Access to the maxillary antrum is enabled from the jaw ridge. The mucous membrane is hereby punched in the toothless region of the jaw ridge with a specifically provided punch (Jesch-Punch) and a blind hole is milled into the bone with a cylindrical milling tool, terminating just below the sinus mucous membrane. The employed punch automatically lifts the mucous membrane disk from the bone and produces a central punch mark for the additional bore (milling). The bore is typically milled antrally (from the ridge) with a cylindrical milling tool (for example with a diameter of 3.5 mm) to about 1 mm below the bonelike floor of the maxillary antrum, wherein the bone thickness is measured in advance using x-rays. Because the sinus mucous membrane must not be damaged by the milling tool, the jawbone must not be fully drilled through with the milling tool, leaving instead a thin bone plate on the floor of the blind hole, with the sinus mucous membrane abutting the backside of the bone plate.

Conventionally, this thin bone plate is then carefully pushed towards the maxillary antrum with a cylindrical instrument, whereby it is pressed towards the maxillary antrum together with the sinus mucous membrane which adheres to it above the bone disk. This "punch through" of the bone disk represents a critical point in the procedure because, if the bone disk is punched too strongly, the sinus mucous membrane is lifted like a tent and tensioned, which may lead to damage. The sinus mucous membrane is then carefully lifted, whereafter the bone replacement material is introduced through the bore into the newly created free space. The implant is then generally anchored directly in the bore.

Although very advanced methods have been developed for detaching the sinus mucous membrane through the small bore (which mostly has a diameter of only approximately 4 mm) in a very gentle manner and sufficiently away from the jawbone, a critical moment remains when the jawbone is punched through, demanding significant experience and particular skill from the physician, so that in spite of the careful attention there remains a residual risk that the sinus mucous membrane is damaged when punching through the bone plate.

To make the sinus lift procedure safer, additional tools would be desirable which would make it easier to penetratingly extend the jawbone bore while reducing the damage risk to the delicate sinus membrane behind the jawbone.

SUMMARY OF THE INVENTION

To this end, the device according to the invention has, a tubular body with a distal working opening and an inlet located opposite the working opening, which inlet is closed by a sealing element that is penetrated by a shaft of a working tool, for example a milling tool, while allowing at least a feed, drive and steering motion of the milling tool, wherein the tubular body is provided with a connection for applying an internal pressure. The tubular body is inserted into the blind hole previously introduced in the jawbone, wherein the distal working opening terminates at the end of the blind hole, so that the interior is essentially sealed. The working medium residing in the interior space of the tubular body, preferably a NaCl solution, can then be pressurized by way of the connection, for example by way of a syringe connected to the connection. The bone disk remaining between the blind hole and the maxillary antrum is now milled down in the region of the working opening with the working tool, which can be controlled from the outside. At the moment when the head of the working tool penetrates the bone and enters the region below the sinus membrane, the overpressure in the interior space of the tubular body causes the working medium to flow through the unobstructed opening, thereby pressing the sinus membrane located behind away from the bone and hence out of the working region of the working tool. The outflow of the pressure medium causes a pressure drop which indicates penetration of the bone and also prevents excessive distention of the sinus membrane.

In an advantageous embodiment of the invention, a feed limit stop which is adjustable on the tubular body in the longitudinal direction and has a seating face for an angle piece driving the working tool may be provided. The feed limit stop may be configured as an adjusting nut, which has a seating face for the angle piece and which can be screwed onto a thread disposed in the region of the inlet on the tubular body. A feed limit stop limits the maximum insertion depth of the working tool and hence facilitates handling the device, with adjustment of the limit stop with an adjusting nut representing a particularly advantageous embodiment, because the feed rate with which milling is performed in the direction of the sinus mucous membrane can be easily and precisely controlled with the adjusting nut. Protection of the sinus mucous membrane is ensured because the feed rate of the milling tool is extremely slow (for example, only about 1 mm/min), and the sinus mucous membrane is distended by the pressure of the working medium already at the smallest bone perforation and is pushed away from the potentially damage-inducing milling tool. After the sinus mucous membrane is distended, it is possible to mill a little bit farther to increase the bone perforation.

In another advantageous embodiment of the invention, if the working tool is a rotatably driven working tool, a sliding element transferring rotation forces may be arranged between an inlet opening of the adjusting nut and the shaft of the working tool. The rotation of the adjusting nut is commensurate with the rotation of the shaft, with the sliding element allowing the shaft to spin. The adjusting nut is then slowly screwed in during the milling operation by the rapidly rotating shaft, so that the feed rate of the milling head is automatically adjusted.

Advantageously, a brake element can operate on the adjusting nut, with the pressing force of the brake element adjustable via an actuator. The feed rate of the adjusting nut can thus be easily controlled. By firmly pressing the brake element, the adjusting nut can also be fixed and prevented from advancing.

In another preferred embodiment of the invention, the actuator may be integrated in a handle extension which projects crosswise or substantially crosswise with respect to the axis of the adjusting nut. The instrument can be more easily handled with the handle extension, whereby in particular the pressing force of the brake element and hence the feed rate can be easily controlled, preferably with one hand, for example with an adjusting screw.

For sealing insertion in the bone bore, the region of the tubular body to be inserted in the blind hole may have a conical shape. The conical region can be pressed into the blind hole by manually applying a force. This is particularly advantageous when a handle extension is provided which hinders rotation of the instrument inserted in the bore inside the mouth.

Rotation of the instrument can be used to screw the instrument into the bore. To this end, in another embodiment, a self-threading exterior thread may be provided on the tubular body in the region to be inserted in the blind hole. This ensures secure retention of the tubular body in the bore and improves sealing against the inner wall of the bore. To further improve sealing, a flange which is adjustable along the tubular body and releasably secured to the tubular body, may be provided on the outside of the tubular body, with the flange having a conical sealing protrusion extending between the tubular body and the wall of the blind hole. The flange is pressed with the cone against the mucus membrane and then fixed, for example with a socket head screw.

According to one embodiment of the invention, a wider handle region may be provided on the tubular body to facilitate handling.

In another advantageous embodiment of the invention, the milling tool may be connected via the connection with a manual or automatic pressure control device. This enables precise control of the interior pressure, whereby penetration of the bone can be readily identified based on the pressure drop.

Advantageously, the sealing element may be formed by one or more O-ring seals. Typically, no stringent requirements are placed on the sealing element, because small leaks are not critical and leaking working medium at the sealing element can be easily compensated by the pressure control device. O-ring seals may therefore be satisfactory for an adequate effect, and thus represent a particularly cost-effective and simple design. In addition, the O-ring seal for the shaft of the working tool operates as a bearing which centers the shaft and which not only allows feed motion, but also a tumbling steering motion of the working tool, without significantly impairing the sealing properties.

In another embodiment according to the invention, the sealing element may be formed by a perforated membrane which can provide similar advantages as the aforementioned O-ring seals, while allowing greater freedom for dimensioning the through-opening for the working tool.

According to the invention, end hooks which protrude over the work opening may advantageously be provided on the end face of the tubular body. The end hooks are used, in addition to the cutting thread, to securely retain the tubular body in the blind hole. Unlike the cutting thread, which is primarily screwed into the soft spongiosa of the jawbone, the end hooks advantageously engage in the compacta of the jawbone in the marginal region of the bone disk remaining on the end of the blind hole.

In the embodiments according to the invention, where a conventional rotatably driven milling tool is used, the sealing element performs the function of a shaft seal and must seal the rotating shaft without restricting its freedom of movement. This places significant demands on the quality of the sealing element and causes rapid wear of the same. The milling head may also touch the inner wall of the tubular body in the region of the working opening, which causes accelerated wear of the milling head as well as increased heat generation. In addition, metal chips which then remain in the surgical area can come loose when the milling head is worn. According to another advantageous embodiment of the present invention, this can be prevented by implementing the working tool as a rotation-free working tool. Rotation-free in the context of the present invention indicates that the working tool and the sealing element contact each other essentially without relative velocities therebetween, because the working tool does not rotate about its major axis. This obviates the need to seal a rotating shaft with a (rotary) shaft seal, thereby reducing the demands on the sealing element.

To transfer work energy to the bone to be removed, the device may advantageously include a device for generating and/or transmitting mechanical or electromagnetic oscillations. The relative movements which can occur when transmitting mechanical oscillations between the working tool and the sealing element are compensated by the elasticity of the sealing element, so that the effect of the sealing element is not significantly impaired for sufficiently small oscillation amplitudes.

In one embodiment of the invention, the working tool may be a piezoelectric, surgical instrument, preferably an ultrasound osteotome. Ultrasound cutting devices for medical applications (other terms are "ultrasound osteotome" or "ultrasound bone mill") are known in the fields of surgical and dental medicine and are in many aspects superior to the conventional rotating instruments, which may be driven with an angle piece. Commercially available ultrasound instruments consist essentially of a hand piece in which an ultrasound transducer is arranged and an extension mounted on the hand piece which is especially designed for the respective application. These systems include as an ultrasound transducer predominantly a piezoelectric oscillator.

The extensions have a shape adapted for the respective application and may have a region incorporating diamonds which affects the cutting properties of the extension. The important settings, in particular the oscillation strength and the frequency (optionally for several oscillation directions, e.g., horizontal and vertical), can be controlled via a control device. In addition, sensors may be arranged in the hand piece, for example for measuring the electric resonance in the hand piece, thereby allowing a more complex control of the operating parameters or detection of changes in the bone structure.

The use of ultrasound osteotomes has the advantage that the instrument only has a cutting or milling effect on hard tissue (bones), whereas the soft tissue (for example the sinus membrane) is not damaged. This ensures high precision and safety with minimal tissue damage. It is also advantageous in the context of the present invention that the shaft of an ultrasound extension does not rotate and can therefore be more easily sealed at the inlet of the tubular body.

The pressure applied on the bone by the ultrasound osteotome is very small, thereby preventing accidental penetration of the bone which could damage the sinus membrane. Because the pressing force when working with the ultrasound osteotome is significantly less than for rotating milling heads, the milling process can more easily be performed "freely", i.e., without a limit stop limiting the penetration depth. Unlike a rotating milling head which can quickly damage the sinus membrane upon contact, the ultrasound osteotome can touch the sinus membrane and even exert pressure on the sinus membrane, without necessarily damaging the sinus membrane.

In a preferred embodiment, the working tool may be an ultrasound osteotome operating in the micrometer range, in particular in a range between 20 and 200 micrometers. Settings can also be provided for the different superpositioned oscillations which the physician can adjust to the respective situations, in particular the condition of the bone to be worked on and the employed ultrasound tip. For example, the effective working oscillation of the hand piece may result from a superposition of a stronger horizontal (60-200 µm) and a smaller vertical (20-60 µm) vibration. The setting selected by the physician ensures that the bone remains clean and is cooled during cutting. Overheating of the tissue can thereby be prevented.

In an alternative embodiment of the invention, the working tool may be a laser cutting tool which may advantageously include a preferably pulsed $CO_2$-laser or solid-state laser. Laser cutting devices for surgical applications allow contactless operation with high position. In particular $CO_2$-lasers with short pulses have proven to be very effective for processing bone material. Excessive heating of the surrounding tissue can be prevented by adjusting the pulse length. Another advantage of laser cutting devices in surgical applications is reduced bleeding, because blood vessels are closed off by the laser.

In another embodiment of the present invention, the wavelength of the laser can be matched to the absorption characteristic of bone tissue. A precisely matched wavelength causes of the laser beam incident on the bone to be absorbed at the surface of the bone in a layer having a thickness of only several micrometers, so that the laser is effective only in this region. Surrounding tissue with a different absorption characteristic can thereby be protected. With respect to a $CO_2$-laser, the most important emission line of the laser may be, for example, between 9 and 11 µm. Optimal absorption by the bone can typically be expected in this range. The term "most important emission line" generally refers to the range where the emission spectrum of the laser has its highest value.

In another embodiment of the present invention, the laser may have adjustable focusing. Focusing limits the effective range of the laser to an adjustable depth. By adjusting the focusing of the laser slowly to deeper regions, one can prevent that the laser unintentionally "shoots through" the sinus membrane as soon as the bone is removed.

According to another advantageous embodiment of the invention, the laser cutting device may be coupled with an endoscope. The rapidly progressing techniques in the development of endoscopy already allow the use of micro-endoscopes with a diameter of 0.5 mm and less. The tip of the laser inserted into the instrument can therefore be additionally provided with an endoscope, whereby optionally the same light guide can be used for the laser and for the endoscope.

BRIEF DESCRIPTION OF THE DRAWING

The invention will now be described in detail with reference to the appended figures.

DETAILED DESCRIPTION OF PREFERRED EMBODIMENTS

Figure 1:
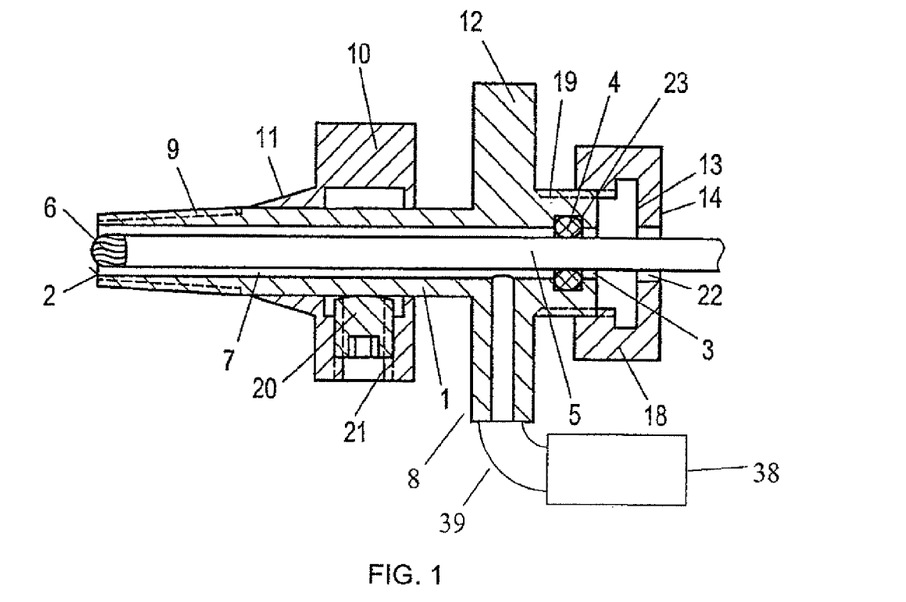
FIG. 1 shows the device according to the invention in a cross-sectional view.
Figure 2:
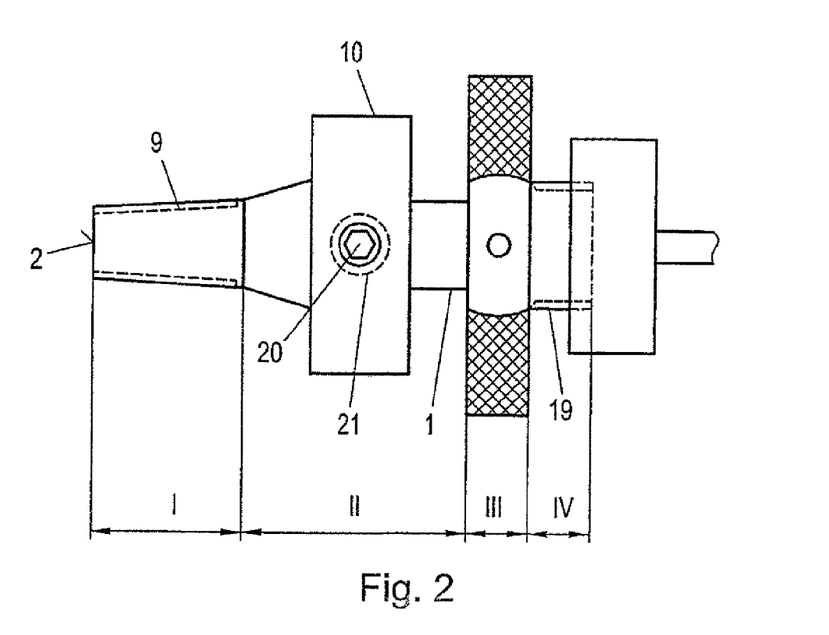
FIG. 2 is a side view of the device.

The device according to the invention illustrated in FIG. 1 in a cross-sectional view, which is once more shown in FIG. 2 in a side view, includes a tubular body 1 having a conically formed tip region with a self-threading exterior thread 9 arranged on the outside of the tubular body 1, with which the tubular body 1 can be screwed into a blind hole provided in the jawbone. The cavity of the tubular body is substantially cylindrical and extends from a working opening 2 on the tip of the tubular body 1 to an inlet 3 formed opposite the working opening 2.

Between the working opening 2 and the inlet 3, the tubular body can be essentially subdivided into four regions: the aforedescribed conical tip region I with the self-threading exterior thread 9, a central cylindrical region II onto which a flange 10 is pushed, a grip region III formed as a retention disk 12, and an end region IV provided with an exterior thread.

The flange 10 pushed onto the cylindrical region II has on its side facing the tip region a conical sealing protrusion 11. A threaded bore 21 into which a socket head screw 20 can be screwed is introduced transversely to the axis of the flange 10 which can be moved along the entire cylindrical region II. When the socket head screw 20 is tightened, it presses against the tubular body 1, thereby fixing the position of the flange 10.

The handle region III is essentially formed as a flat retention disk 12 which preferably has along its peripheral surface a serration to facilitate gripping the small instrument as well as screwing in and unscrewing the small instrument. The retention disk 12 has a thin bore which is drilled through to the cavity of the tubular body 1 from the side and represents a connection 8. A hose 39 running to a syringe or a manual or automatic pressure control device 38 can be attached to this connection 8, wherein a working medium can be introduced into the cavity of the tubular body 1 through this connection 8.

An adjusting nut 18 having a feed limit stop 19 with a seating face 14 arranged on the side facing away from the tubular body 1 is screwed onto the exterior thread 19 of the end region IV. The seating face 14 can be adjusted by rotating the adjusting nut 18. To enable fine adjustment of the seating face, the exterior thread 19 is preferably implemented as a fine thread. The feed limit stop 13 has in the center of the seating face 14 an entrance opening 22 extending to the cavity of the tubular body 1, through which a shaft 5 of a milling tool 5, 6 is introduced into the cavity of the tubular body 1. The diameter of the entrance opening 22 is slightly greater than the diameter of the shaft 5 of the milling tool 5, 6, so that the milling tool 5, 6 is movable inside the tubular body 1.

To form a pressure chamber 7 inside the tubular body 1, the cavity of the tubular body 1 and the shaft 5 of the milling tool 5, 6 must be sealed in the region of the inlet 3. In the embodiment illustrated in FIG. 1, the sealing element 4 is a simple O-ring seal which is arranged in an annular groove 23 disposed inside the cylindrical cavity of the tubular body. Because absolute leak tightness of the pressure chamber 7 is not required, as will be described in more detail below, this particularly simple sealing arrangement is generally sufficient to ensure the functionality of the device. However, if desired, other conventional sealing arrangements may be used.

Figure 3:
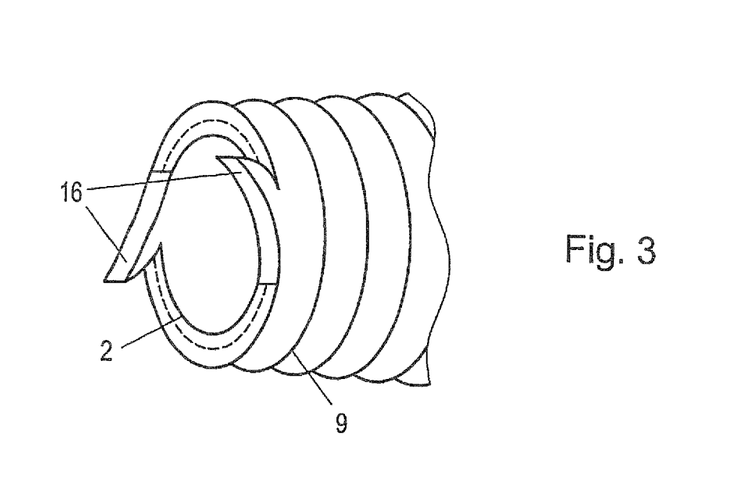
FIG. 3 shows in form of a diagram the tip of the device with the protruding end hooks.

According to another preferred embodiment of the invention, end hooks 16 can be provided on the tip of the tubular body 1, as illustrated in FIG. 3. The end hooks 16 shown in FIG. 3 correspond essentially to an "extension" or "offshoots" of the thread stages or cutting edges of the self-threading exterior thread 9, wherein the end hooks 16 protrude over the end of the tubular body 1 at the edge of the working opening 2. When the tubular body 1 with the self-threading exterior thread 9 is screwed into the prepared blind hole, the end hooks 16 bore into the bone plate remaining behind the blind hole, thereby ensuring secure retention of the device. This is particularly advantageous because the bone tissue is a firmer in the marginal region of a bone (the so-called substantia compacta) than in the central bone region (spongiosa), and the end hooks 16 engage exactly in this marginal region.

Figure 4:
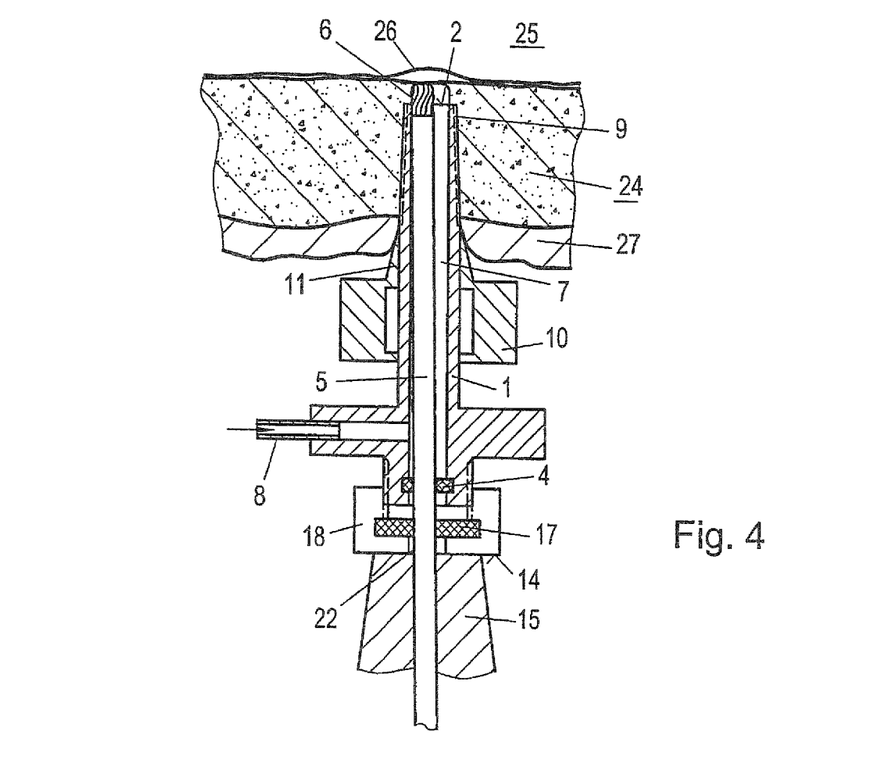
FIG. 4 is a cross-sectional view of the device according to the invention inserted in a jawbone.
Figure 5:
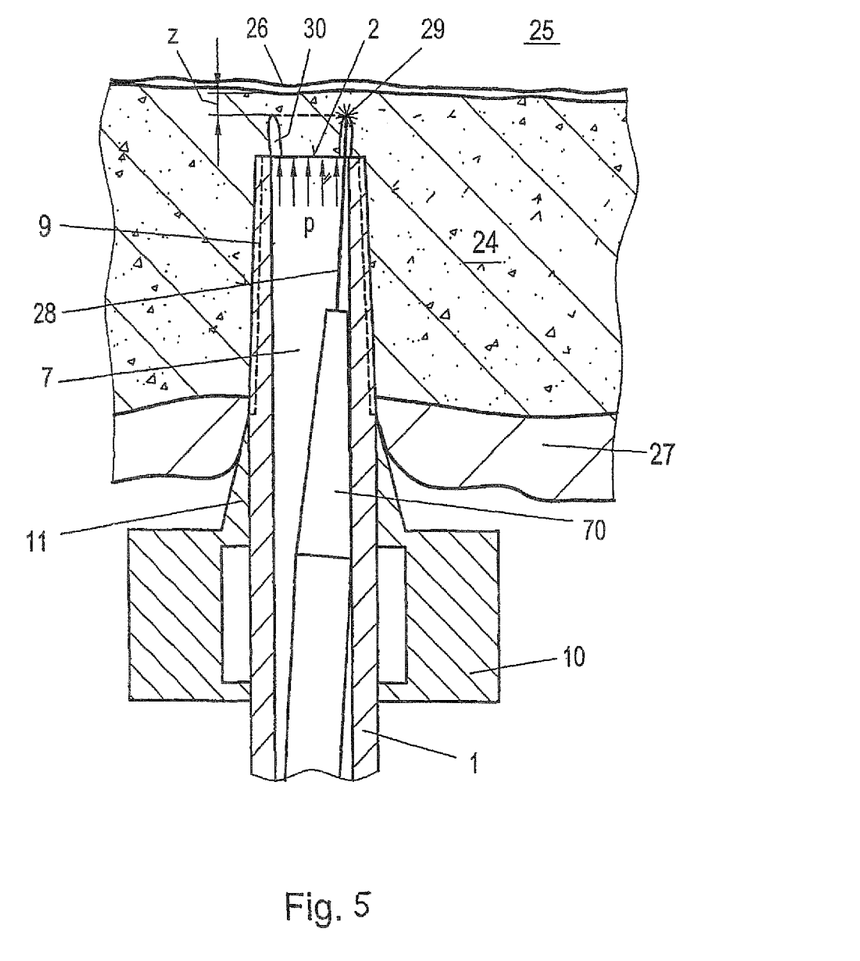
FIG. 5 illustrates the use of a laser osteotome.

The use of the device according to the invention will now be described more particularly with reference to FIG. 4, wherein FIG. 4 shows the device of the invention during a sinus lift at the moment when the milling head 6 of the milling tool 5, 6 penetrates the jawbone.

Like with the conventional crestal sinus lift, a blind hole is initially introduced from the jaw ridge into the jawbone 25, leaving an approximately 1 mm deep bone plate between the end of the blind hole and the maxillary antrum 25. This is necessary to prevent damage to the sinus mucous membrane 26 which contacts the jawbone 24 and the maxillary antrum 25. The tubular body 1 with the self-threading exterior thread 9 is then screwed into the prepared blind hole, until the working opening 2 touches the bone plate, whereby the self-threading exterior thread 9 and the end hooks 16 ensure firm retention of the tubular body 1.

To improve the sealing effect, the flange 10 is then moved on the tubular body 1 towards the jawbone, so that the conical sealing protrusion 11 arranged on the flange 10 is firmly pressed against the mucous membrane 27 at the outer edge of the blind hole, thereby sealing the bore. Optionally, a rubber dam may also be used.

The milling tool 5, 6 clamped on an angle piece 15 is inserted in the tubular body 1 through the entrance opening 22 and the sealing elements. The length of the shaft 5 of the clamped milling tool 5, 6 (or the length of the tubular body 1, respectively) is dimensioned so that the tip of the milling head 6 of the milling tool 5, 6 engages with the bone plate when the angle piece 15 abuts the seating face 14 of the adjusting nut 18.

The device illustrated in FIG. 4 has, in addition to the O-ring seal in the tubular body 1, as an additional sealing element a perforated membrane 17 which is arranged inside the adjusting nut 18 and seals the shaft 5 of the milling tool 5, 6 at the entrance opening. The pressure chamber 7 may also only be sealed, for example, by a perforated membrane 17 which is directly arranged at the inlet 3 of the cavity of the tubular body 1. Several sealing elements may also be sequentially arranged in the tubular body 1, as long as they have sufficient elasticity to allow easy pivoting of the shaft 5 of the milling tool 5, 6, so that the head of the milling tool 5, 6 can move in the entire range of the working opening 2.

The cavity of the tubular body 1 is hence sealed on both ends of the tubular body, thereby forming a pressure chamber 7 to which a working medium can be applied via the connection 8. In the simplest case, a NaCl solution can be pressed into the pressure chamber with a syringe or a hose. However, the supply may also occur via an electric pump, wherein the prevailing pressure, for example about 0.5 to 2 bar, can be measured and displayed.

The remaining bone plate is then slowly removed with milling tool 5, 6 by a circular motion of the milling head 6, wherein the feed rate of the milling tool 5, 6 is controlled via the adjusting nut 18, so that a very slow advance, for example 1 mm/min, can be attained. The working medium in the pressure chamber 7 is also used to remove the heat generated during the milling operation and operates as a lubricant on the sealing element 4 for the rotating shaft 5. Small quantities of the working medium which can leak from the rotating shaft 5 in spite of the sealing element 4, do not represent a problem because the pressure of the working medium in the pressure chamber 7 can be maintained via the connection 8. Good sealing properties of the sealing element 4 are nevertheless advantageous, because the pressure drop at the moment of penetration of the bone disk can be more easily detected with a leak-tight pressure chamber 7.

As soon as the milling head 6 drills through the bone disk, the pressurized working medium flows through the produced opening and lifts the sinus mucous membrane 26 located behind the bone disk in form of a bubble. This corresponds to the situation illustrated in FIG. 4. The sinus mucous membrane 26, which must be preserved, is hence automatically pushed out of the danger zone represented by the rapidly rotating milling head 6.

After the bone disk has been milled through, the edge of the bore can be somewhat further machined with the milling tool 6, because the sinus mucous membrane 26 remains lifted in form of a bubble. The sinus mucous membrane 26 can also be detached further with the working medium by carefully pressing working medium into the pressure chamber and thus also into the cavity underneath the sinus mucous membrane 26. The instrument according to the invention is then again unscrewed from the bore. If necessary, the sinus mucous membrane 26 can be further detached and lifted by using other methods before the bone replacement material is introduced and the implant is screwed into the bore.

The invention is therefore based on the idea that the blind hole is continuously subjected to a hydrostatic pressure when the bone of the maxillary antrum is initially opened towards the sinus mucous membrane, causing the sinus mucous membrane to lift off during the smallest first perforation of the bone and to retreat or "flee" from the milling tool. As will be described below, the initial opening in the bone cannot only be created with a milling tool, but for example also with other surgical instruments, for example a drill, an ultrasound piezoton or a ($CO_2$) laser.

FIG. 2 shows the tip of another embodiment of the present invention. Instead of the mechanical removal of the bone material, the jawbone 24 is machined with a laser osteotome 70. The part of the laser illustrated in FIG. 2 may be, for example, the end of a light guide through which the laser beam is introduced in the instrument. The light guide is thin enough so that it can be pushed into the pressure chamber 7 of the tubular body 1. Sealing is performed similar to the other described embodiments.

Due to the conical shaped of the tip of the light guide, the laser beam 28 can be accurately guided to the edge of the working opening 2 by contacting the inner wall of the tubular body 1 with the light guide. Through circular movements with the laser osteotome 70, the path of the point 29 where the laser beam 28 is incident on the bone mills an annular groove 30 into the bone.

The distance between the effective point of the laser beam and the tip of the laser osteotome 70 can be exactly determined by using a focused laser. The milling operation can be precisely controlled either by adjusting the focusing or by slowly advancing the laser osteotome 70. Due to the exactly defined working depth of the laser, the annular groove 30 can be widened until it almost reaches the sinus membrane 26, without damaging the sinus membrane.

As soon as the distance z between the sinus membrane 26 and the end of the annular groove 30 is less than a predetermined thickness, the jawbone 24 breaks through along the annular groove 30 as a result of the interior pressure p in the pressure chamber 7, which is greater than the pressure in the maxillary antrum 25, even before the penetration depth of the laser has reached the sinus membrane 26. The "critical" thickness z depends here on the bone condition, the area of the working opening and the pressure p in the pressure chamber.

The breakthrough through the bone plate can be detected by the accompanying pressure drop in the pressure chamber, wherein optionally the pressure drop can trigger an automatic turnoff of the laser.

Optionally, the laser osteotome 70 may be coupled to a miniature endoscope, so that progress of the surgical procedure and in particular breakthrough of the bone plate can be optically monitored.

Figure 6:
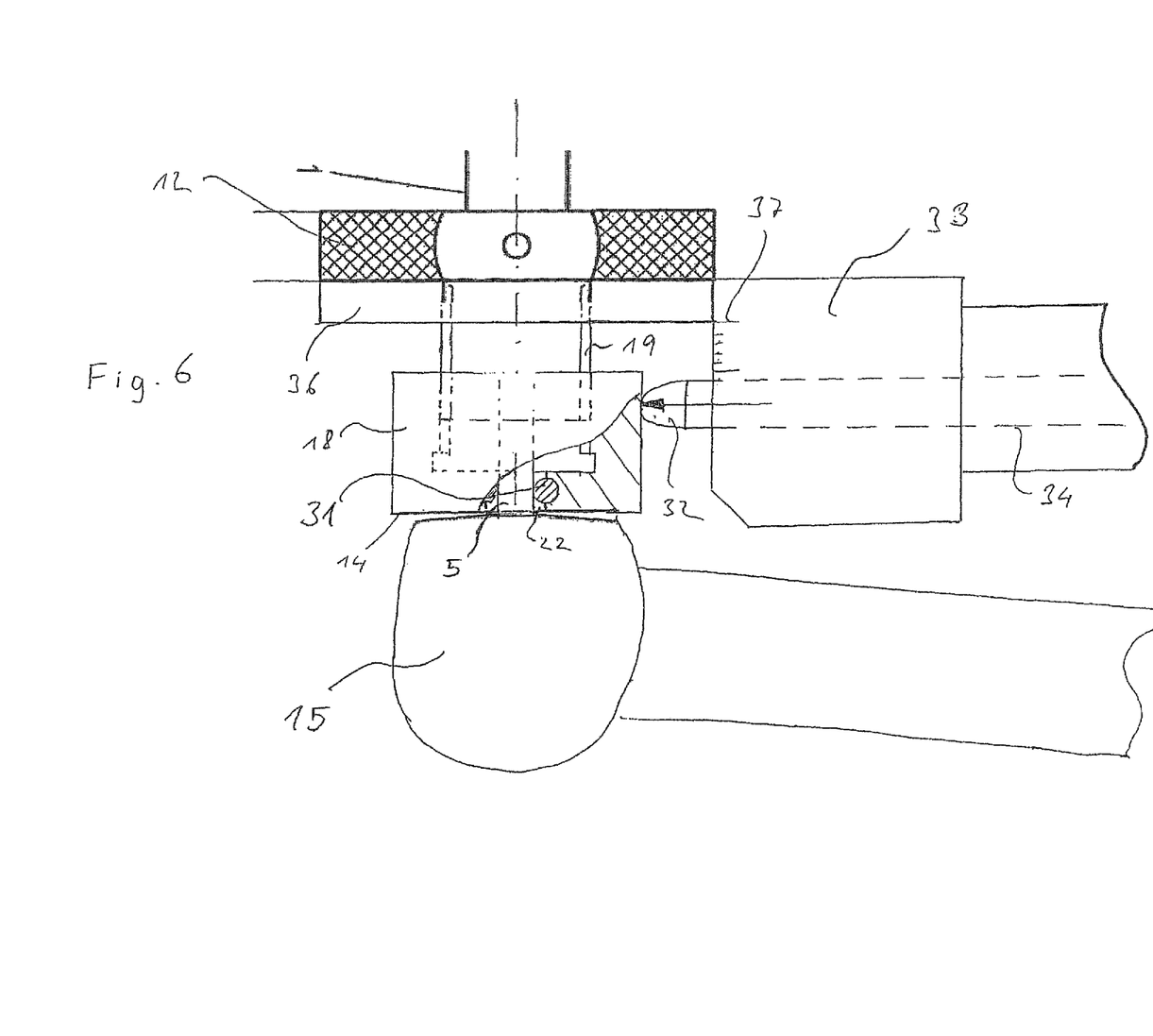
FIG. 6 shows a device with an automatically driven adjusting nut.

FIG. 6 shows another advantageous detail of the invention which allows an easily controllable feed rate for the milling tool. A handle extension 33 is arranged on the instrument in the region of the retention disk 12 of the attachment protrusion 36. The attachment protrusion 36 is screwed onto the exterior thread 19 of the end region IV of the tubular body 1 and abuts the retention disk 12. However, the handle extension 33 or the attachment protrusion 36 may also be secured in a different way, for example by a clamping arrangement; optionally, the handle extension could also be formed as a single piece with the instrument.

A sliding element 31 is arranged in the interior of the adjusting nut 18 in the entrance opening 22, wherein the sliding element 31 provides dynamic friction between the rotating shaft 5 and the adjusting nut 18. The sliding element may preferably be as simple O-ring which applies only a small pressure onto the shaft 5, so that the shaft 5 rotates with high slippage in the O-ring and only transfers very small rotational energy to the adjusting nut 18. The dynamic friction drives the adjusting nut 18, which is thereby slowly screwed in over the exterior thread 19, so that the stop face 14 and thus the advance of the milling head are also moved. Optionally, the sliding element 31 can replace the sealing element 4 in the tubular body.

A brake element 32 operates on the adjusting nut 18, wherein the brake element 32 presses against the cylindrical exterior surface of the adjusting nut in the direction of the arrow via a brake rod. By adjusting the pressing force, the rotation of the adjusting nut 18 can be more or less slowed down or stopped.

Figure 7:
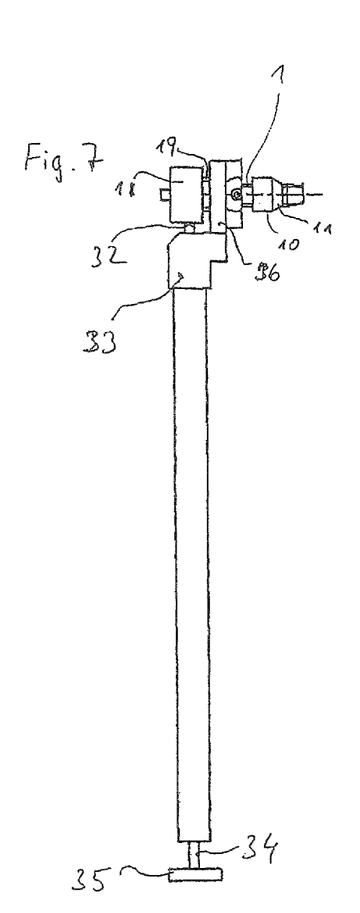
FIG. 7 shows the device with an attached handle extension in a side view.
Figure 8:
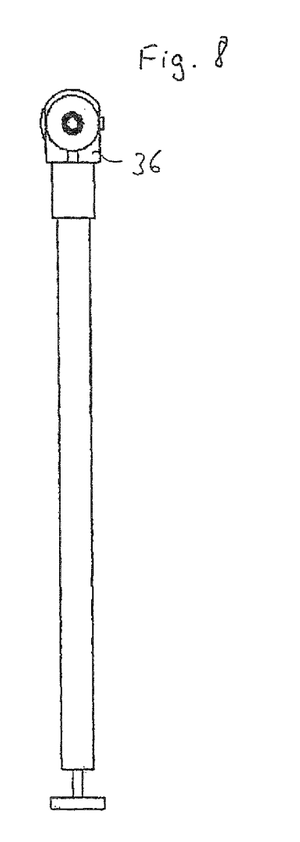
FIG. 8 shows the same device in a top view.

The handle extension 33 is once more completely illustrated in FIGS. 7 and 8, wherein a readily accessible thumb wheel 35 is arranged on the end of the brake rod 34 facing the brake element 32, with which the brake rod can be screwed in and unscrewed via a thread (not shown) disposed inside the handle extension. The thumb wheel 35 can be operated by the operator with one hand, while the other hand operates in the angle piece.

At the beginning of the milling operation, the brake is firmly tightened, so that the stop face 14 has a predetermined spacing from the working opening 2, thereby preventing the milling head 6 from entering the jawbone deeper than planned. To advance deeper towards the maxillary antrum with the milling head, the operator releases the brake by turning the thumb wheel 35, so that the adjusting nut 18 is rotated to a certain extent together with the milling tool shaft 5 and screwed in, whereafter the brake is tightened again. The physician can control the set advance by observing the adjusting nut, wherein a scale 37 can help with estimating the insertion depth. The scale can be arranged either on a part of the handle extension or at another location of the instrument.

The invention claimed is:

1. A device for penetratingly extending a blind hole introduced into hard tissue, particularly a jawbone, comprising:
   a tubular body having a distal working opening and an inlet opposite the working opening, wherein the tubular body is either constructed to be sealingly inserted into a bone bore or wherein the tubular body comprises means for sealing insertion into the bone bore, a sealing element in cooperation with a shaft of a rotatably driven milling cutter said shaft penetrating the sealing element, closing the inlet of the tubular body, while allowing at least a feed motion, a drive motion and a steering motion of the rotatably driven milling cutter, a connection disposed on the tubular body and opening into the tubular body at a proximal end of the tubular body for applying a pressure above atmospheric pressure in the tubular body; and a pressure control device connected to the tubular body via the connection, said pressure control device constructed to generate the pressure above atmospheric pressure.

2. The device of claim 1, further comprising a feed limit stop, which is adjustable on the tubular body in a longitudinal direction and has a seating face for an angle piece driving the milling cutter.

3. The device of claim 2, wherein the tubular body comprises a thread disposed in a region of the inlet and the feed limit stop is constructed as an adjusting nut which can be screwed onto the thread.

4. The device of claim 3, further comprising a sliding element transferring rotation forces between an entrance opening of the adjusting nut and the shaft of the milling cutter.

5. The device of claim 4, further comprising a brake element operating on the adjusting nut and applying a pressing force on the adjusting nut, wherein the pressing force is controllable via an adjusting device.

6. The device of claim 5, further comprising a handle extension protruding from the device crosswise or substantially crosswise with respect to an axis of the adjusting nut, wherein the adjusting device is integrated in the handle extension.

7. The device of claim 1, wherein the tubular body has a self-threading exterior thread in a region of the tubular body to be inserted into the blind hole.

8. The device of claim 1, wherein the means for sealing insertion into the bone bore is constructed as a flange disposed outside the tubular body and has a conical sealing protrusion extending between the tubular body and a wall of the blind hole, said flange being adjustable along the tubular body and releasably secured to the tubular body.

9. The device of claim 1, the tubular body further comprising a handle region.

10. The device of claim 9, wherein the handle region is constructed as a retaining disk.

11. The device of claim 1, further comprising a connection connected with a manual or an automatic pressure control unit for applying the internal pressure.

12. The device of claim 1, wherein the sealing element is formed by one or more O-ring seals.

13. The device of claim 1, wherein the sealing element is formed by a perforated membrane.

14. The device of claim 1, further comprising end hooks arranged on an end face of the tubular body and protruding over the distal working opening.

* * * * *